United States Patent [19]

Hemmer

[11] Patent Number: 5,334,168
[45] Date of Patent: Aug. 2, 1994

[54] VARIABLE SHAPE GUIDE APPARATUS

[75] Inventor: Chad G. Hemmer, Indianapolis, Ind.

[73] Assignee: Catheter Research, Inc., Indianapolis, Ind.

[21] Appl. No.: 76,113

[22] Filed: Jun. 11, 1993

[51] Int. Cl.$^5$ .................. A61M 25/00; A61M 37/00
[52] U.S. Cl. .................................. 604/281; 604/95
[58] Field of Search .................. 604/95, 280–282; 128/45 M

[56] References Cited

U.S. PATENT DOCUMENTS

| | | | |
|---|---|---|---|
| 3,868,956 | 3/1975 | Alfidi et al. | 606/194 |
| 4,543,090 | 9/1985 | McCoy . | |
| 4,601,705 | 7/1986 | McCoy . | |
| 4,758,222 | 7/1988 | McCoy . | |
| 4,790,624 | 12/1988 | Van Hoye et al. | 350/96.26 |
| 4,799,474 | 1/1989 | Ueda | 128/4 |
| 4,944,727 | 7/1990 | McCoy . | |
| 4,950,258 | 8/1990 | Kawai et al. | 604/281 |
| 5,019,040 | 5/1991 | Itaoka et al. | 604/95 |
| 5,114,402 | 5/1992 | McCoy . | |
| 5,135,517 | 8/1992 | McCoy . | |
| 5,188,111 | 2/1993 | Yates et al. . | |
| 5,242,394 | 9/1993 | Tremulis . | |

FOREIGN PATENT DOCUMENTS

| | | | |
|---|---|---|---|
| 4028375 | 1/1992 | Japan | 604/281 |
| 4051967 | 2/1992 | Japan | 604/281 |
| 1204216 | 1/1986 | U.S.S.R. | 604/281 |

*Primary Examiner*—John D. Yasko
*Assistant Examiner*—Adam J. Cemak
*Attorney, Agent, or Firm*—Barnes & Thornburg

[57] ABSTRACT

An apparatus includes a flexible, elongated tubular member and a tube arranged to lie inside the tubular member. The tube has a lumen extending along the central axis of the tubular member. In one embodiment, the tube is made of a temperature-activated shape memory metal. In another embodiment, the tube is made of superelastic nitinol.

13 Claims, 1 Drawing Sheet

VARIABLE SHAPE GUIDE APPARATUS

BACKGROUND AND SUMMARY OF THE INVENTION

The present invention relates to catheters, cannulae, and the like, and particularly to apparatus that are steerable through body cavities and aimable at obstructions, organs, or tissue within the body from a position external to the body. More particularly, the present invention relates to nitinol tubing for medical devices, including steerable and aimable apparatus.

A great deal of research effort has focused on providing a catheter having a distal end which, when inserted into a body, is readily steerable and aimable to advance the catheter through body cavities and passageways. It has been observed that materials exhibiting mechanical memory properties triggered by heat are particularly useful for enhancing the maneuverability of catheters or like devices. The materials are commonly called "temperature-activated memory materials" or "shape memory alloys" because they move to assume a predetermined shape when heated to a predetermined temperature.

Nitinol, a nickel-titanium alloy, is one such temperature-activated memory material that has been formed into memory element strips and deployed in the distal end of a catheter. Heating the nitinol memory element strips to a given temperature using an electric current provided by a power supply causes the memory elements to deform to assume a predetermined shape, thereby deflecting the distal end of the catheter. See, for example, U.S. Pat. Nos. 4,543,090; 4,601,705; and 4,758,222 for descriptions of known memory element systems for steering and aiming catheters, cannulae, and the like.

Use of shape memory nitinol has previously been used in "strip" or "rod" form in the construction of steerable and aimable apparatus. Such nitinol strips and rods are solid core elements having a circular, rectangular, or other similar cross-sectional shape. In use, these solid core memory element strips or rods are placed on opposing sides of a central lumen formed in an apparatus about the circumference of the apparatus. Selective activation of these memory element strips or rods results in articulation of the apparatus. See, for example, U.S. Pat. No. 4,601,705 for a disclosure of a four-memory element strip steering and aiming system and U.S. Pat. No. 4,758,222 for a disclosure of a steering and aiming system using a spring and one temperature-activated memory element strip.

What is needed is an improved system for steering and aiming an apparatus quickly and effectively without using multiple memory elements or springs. Such an improved steerable and aimable apparatus would, for example, reduce the complexity of the assembly by using fewer pieces.

According to the present invention, a steerable and aimable apparatus includes a flexible, elongated tubular member and a nickel titanium tube. The tubular member has a central axis extending longitudinally therethrough and the nickel titanium tube is formed to include a lumen extending along the central axis. Control means is also provided for selectively heating the nickel titanium tube to move the nickel titanium tube to assume a predetermined shape, thereby moving the tubular member so that it assumes a corresponding predetermined shape.

In one preferred embodiment, the tubular member includes an outer sleeve and an inner sleeve and the nickel titanium tube is sandwiched between the inner and outer sleeves. The inner sleeve is formed to include a through lumen and the control means is operated to heat the nickel titanium tube enough to bend the inner and outer sleeves simultaneously.

In another preferred embodiment, the tubular member includes a cylindrical interior side wall defining a passageway extending longitudinally along the central axis. The nickel titanium tube includes an exterior side wall extending longitudinally along the central axis of the tubular member and engaging the interior side wall of the tubular member. The nickel titanium tube is formed to include a lumen extending along the central axis of the tubular member. Essentially, the main lumen for the apparatus is provided by the nickel titanium tube itself.

Nickel titanium tubing can also be used in pairs to control articulation of a steerable and aimable apparatus in accordance with the present invention. In this embodiment, a pair of nitinol tubes is arranged inside a tubular member in spaced-apart parallel relation on opposite sides of a longitudinally extending lumen. One nitinol tube can be activated to bend the tubular member in a first direction. Alternatively, the other nitinol tube can be activated to bend the tubular member in an opposite second direction.

Advantageously, the improved apparatus is steered and aimed using a nitinol tube instead of solid core nitinol strip or rod. This apparatus is easier to manufacture and assemble.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
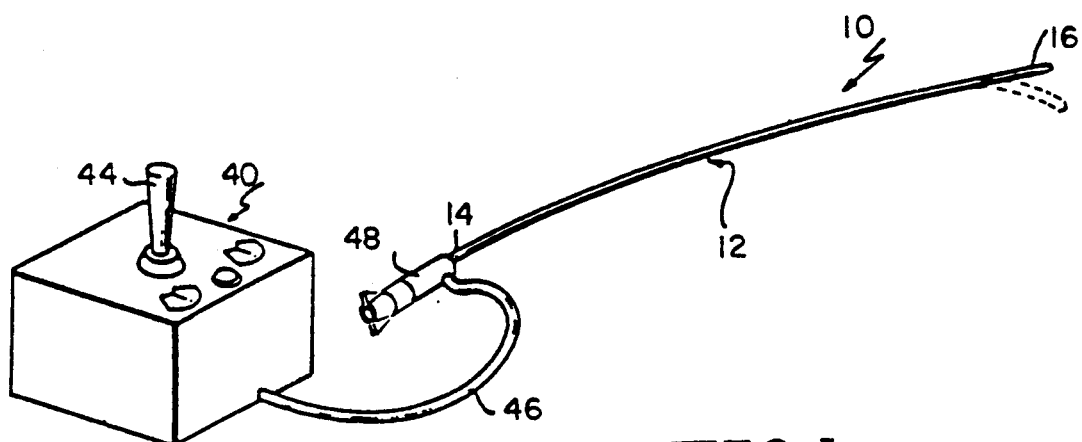
FIG. 1 is a perspective view of a steerable and aimable apparatus embodying the present invention.

An apparatus 10 embodying the present invention is shown generally in FIG. 1. Apparatus 10 includes an elongated tubular member 12 having a proximal end 14 and a steerable and aimable distal end 16. In the illustrative embodiment, the tubular member 12 is formed of plastic, TEFLON® material, silicone, nylon, cross-linked polyethylene, or other similar material. It is desirable that tubular member 12 be formed of a material that is flexible, can withstand heat, and which provides electrical insulation.

Figure 3:
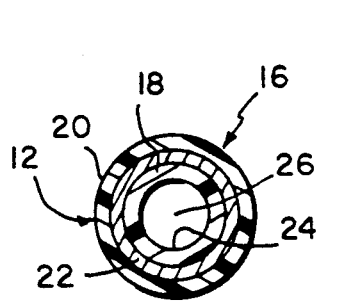
FIG. 3 is a transverse sectional view taken along line 3—3 of FIG. 2 showing the nitinol tube sandwiched between an inner and outer sleeve of the tubular member.
Figure 2:
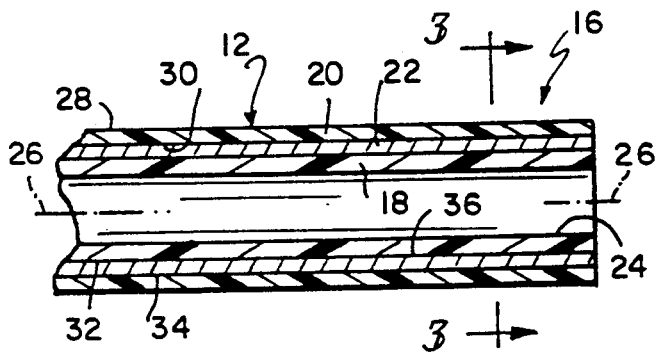
FIG. 2 is an enlarged view of one portion of the distal end of one embodiment of the apparatus in FIG. 1 showing a single nitinol tube encased in a tubular member.

Illustratively, tubular member 12 is formed as shown in FIGS. 2 and 3 to include an inner sleeve 18, an outer sleeve 20, and a nickel titanium tube 22 sandwiched between the inner and outer sleeves 18 and 20. A source of nitinol tubing is Innovation Technology International of Beltsville, Md. The inner sleeve 18 is formed to include a lumen 24 that serves as the main lumen for the tubular member 12. For example, medical instruments (not shown) can be passed back and forth through lumen 24 while the tubular member 12 lies in the body to treat a portion of the body. Also, various fluids (not shown) can be injected into or drained from a body cavity (not shown) using lumen 24.

The nickel titanium tube 22 is arranged to extend longitudinally along a central axis 26 of the tubular member 12. The outer sleeve 20 includes a cylindrical exterior surface 28 and a cylindrical interior side wall 30 defining a passageway through the outer sleeve 20. The inner sleeve 18 includes a cylindrical exterior surface 32 and a cylindrical interior surface defining the boundary of lumen 24. The nickel titanium tube 22 includes a cylindrical outer wall 34 engaging the cylindrical interior side wall 30 of outer sleeve 20 and a cylindrical inner wall 36 engaging the cylindrical exterior surface 32 of inner sleeve 18.

Illustratively, the inner sleeve 18 and the outer sleeve 20 are made of silicone, PEBAX® material, nylon, or other similar material. Any of the following methods or a combination could be used to fix nickel titanium tube 22 in the position shown in FIG. 2 between the inner and outer sleeves 18 and 20: heat shrink tubings, fusing inner and outer sleeves 18 and 20, dipping, coextrusion, enamel coating, etc. The tube 22 itself can be held (fixed) using adhesives, solder, or mechanically interlocking features. The surface of the nickel titanium tube can also have contours, toughened surface, etc. for increased adhesion (locking) to the surrounding layer(s).

Nickel titanium tube 22 is a temperature-activated memory element that is isolated from a body cavity (not shown) by insulative material (e.g., tubular member 12). The tube 22 exhibits a memory characteristic in response to temperature changes. Instead of being a solid core wire or flat strip, tube 22 is formed in a tubular shape of a mechanical memory metal such as a nickel titanium alloy. While a nickel titanium alloy is desirable, other metal elements having a memory characteristic related to temperature could be used without departing from the scope of the invention. Such metal elements have a high resistance to electric current so that heat is produced when current is passed therethrough.

The nickel titanium tube 22 has a first or preset shape (not shown) and a second shape as shown in FIGS. 2 and 3. Preferably, the preset shape is an arcuate shape, and the second shape is a straight shape. It will be appreciated that the present shape could be any shape. Reference is hereby made to U.S. Pat. No. 4,944,727 for a more detailed description of suitable techniques for providing temperature-activated memory elements that are movable between arcuate and straight shapes. The '727 patent is incorporated by reference herein.

The temperature-activated nickel titanium tube 22 is originally annealed into its arcuate preset shape. The tube 22 is then cooled and straightened to its second shape before incorporation into the distal end 16 of the tubular member 12. When the tube 22 is again heated to a predetermined transitional temperature, it returns to its preset shape. By applying an opposing force to a tube 22 that has moved to assume its preset shape, it can be moved to its second shape. In the illustrative embodiment, the predetermined transitional temperature is any temperature above body temperature. For example, the predetermined transitional temperature may be in the range of 100° F. to 160° F.

The apparatus 10 further includes an electronic control system 40 for controlling current flow to vary the temperature of the temperature-activated nickel titanium tube 22 from a position external to the body so as to deflect the distal end 16 of the tubular member 12 in different directions corresponding to the preset shape of the tube 22. The control system 40 includes a power supply source (not shown) which may be either AC or DC. The system 40 also includes a control device 44 which, in the illustrative embodiment, is similar to a "joystick" control, tactile membrane switch, or ball controller. It will be appreciated that various types of control devices 44 may be employed without departing from the scope of the present invention. Reference is hereby made to U.S. Pat. No. 5,188,111 for more detailed descriptions of suitable control systems for guiding steerable and aimable apparatus. The '111 patent is incorporated by reference herein.

The power supply source is coupled through control device 44 to the tubular member 12 by cable 46 and a coupling device 48. Further, the temperature-activated nickel titanium tube 22 is electrically connected to the control device 44 through cable 46 and coupling 48 by an electrical wire (not shown) which is attached to the tube 22 by conventional means such as soldering, crimping, welding, or electrically conductive adhesive. A return or ground wire (not shown) is attached to the tube 22 by conventional means such as soldering, crimping, welding, or electrically conductive adhesive.

Figure 5:
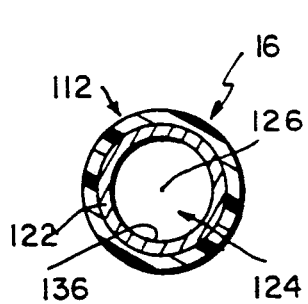
FIG. 5 is a transverse sectional view taken along line 5—5 of FIG. 4 showing a nitinol tube positioned inside a tubular member and formed to provide a through lumen for the apparatus.
Figure 4:
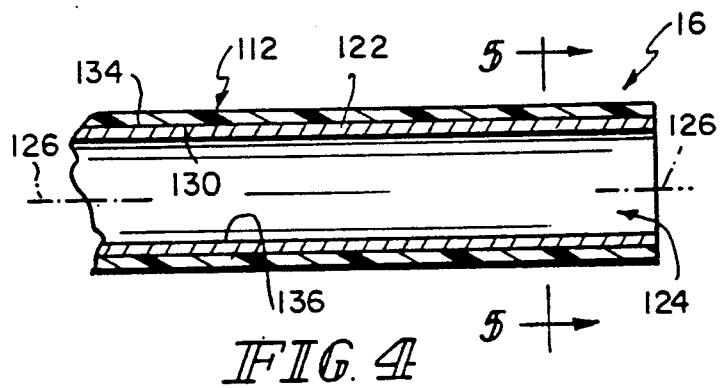
FIG. 4 is an enlarged view of one portion of the distal end of another embodiment of the apparatus in FIG. 1 showing a single nitinol tube inside a tubular member.

In the embodiment shown in FIGS. 4 and 5, tubular member 112 is formed to include a passageway extending along central axis 126 and nickel titanium tube 122 is mounted in that passageway. The cylindrical outer wall 134 of tube 122 engages the cylindrical interior side wall 130 of tubular member 112. The tube 122 is formed to include a cylindrical inner wall 136 which defines the primary lumen 124 of the tubular member 112.

In this embodiment, nickel titanium tube 122 is made, for example, of superelastic nitinol. It will be understood that control means is not needed to heat superelastic nitinol since it is already in an activated (above transition) temperature. For example, a superelastic nitinol tube 122 is formed in a present curved shape and a guide wire (not shown) is used to return the nitinol tube 122 to a straight shape.

Development of this improved apparatus 10 was undertaken for a number of reasons. One objective was to use the variable shape properties of nitinol while providing a through-lumen in a catheter or other steerable and aimable apparatus. It was also a goal to reduce complexity of assembly by using one continuous piece of nitinol rather than a multiplicity of nitinol elements around the perimeter of a catheter. Still another objective was to use the pseudo-elastic properties of superelastic nitinol (SEN) for axial push and flexibility, while providing a through-lumen. These properties typically provide a better combination than stainless steel, which is commonly used in medical devices (e.g., balloon catheters, guide wires, etc.).

The improved apparatus 10 capitalizes on two distinct properties of nitinol tubing: (1) the shape memory property (SMA), and (2) the superelastic behavior (SEN). The shape memory properties allow for variable control of physical shape (recovery) upon activation of the nitinol tube. A predetermined shape can be trained into the nitinol tube (curved, straight, planar, three-dimensional, etc.) prior to final assembly into a catheter, guide wire, or other apparatus. Later, during use, the nitinol tube can be deformed, below its activation temperature, into a shape other than its trained shape. Then, the nitinol tube can be used to cause the catheter to return to predetermined shape.

A tube formed from superelastic nitinol permits the fabrication of a shaft which has significant axial push and flexibility along the shaft length (bending) while exhibiting excellent torque transmission from a proximal end to a distal end and providing a through-lumen. In a finished catheter, this through-lumen could be used for numerous uses, including, but not limited to, inflation/deflation of an angioplasty balloon catheter; injection of drugs or fluids; and insertion of other catheters, fiberscopes, laserfibers, etc. The significance of a nitinol tube over other materials, such as stainless steel, is the ability to have a tube which has torqueability within a flexible, yet pushable, shaft. Stainless steel, for instance, does not transmit torque as well when the tube is long and has a large number of flexures along its length, nor does it transmit axial push force as well from proximal to distal.

Figure 6:
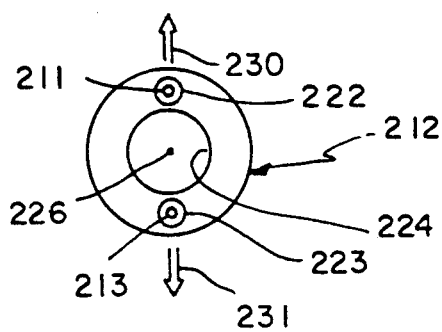
FIG. 6 is a transverse sectional view of another tubular member showing use of a pair of spaced-apart off-center nitinol tubes arranged on either side of an inner lumen.

As shown in FIG. 6, a pair of nitinol tubes 222, 223 can be mounted on opposite sides of a central lumen 224 provided in tubular member 212. A wire 211 can pass through the lumen of tube 222 to conduct electricity to tube 222 and another wire 213 can pass through the lumen of tube 223 to conduct electricity to tube 223. In contrast to the embodiments illustrated in FIGS. 2-5, the nitinol tubes 222, 223 do not have to be arranged in coaxial relation to the flexible tubular member 212. One or more nitinol tubes could be placed in tubular member 212 in offset relation to the central axis 226 of tubular member 212.

It is within the scope of the present invention to make nitinol tubing that has a negative coefficient of thermal expansion so that it shortens upon heating. In such an embodiment, opposite ends of the nitinol tubing would be anchored into the surrounding plastic matrix provided in the tubular member. By placing a nitinol tube off-center and selectively shortening it, the tubular member will bend toward the side the tube is placed upon (e.g., activate tube 222 to bend tubular member in direction 230 or tube 223 to bend tubular member in direction 231. A plurality of nitinol tubes can be placed about the central axis of the tubular member, resulting in a plurality of motion possibilities. Reference is hereby made to U.S. Pat. No. 4,944,727 for a description of nitinol tubing that varies in length upon being heated.

Although the invention has been described in detail with reference to the illustrated preferred embodiments, variations and modifications exist within the scope and spirit of the invention as defined in the following claims.

I claim:

1. An apparatus comprising
   a flexible, elongated tubular member having a central axis extending longitudinally therethrough,
   a nickel titanium tube arranged in the tubular member to extend along the central axis of the tubular member and formed to include a lumen extending therethrough, and
   control means for selectively heating the nickel titanium tube to move the nickel titanium tube to assume a predetermined shape, thereby moving the tubular member so that it assumes a corresponding predetermined shape.

2. The apparatus of claim 1, wherein the nickel titanium tube includes a cylindrical inner wall defining the boundary of the lumen and the apparatus further comprises a tubular insulative sleeve positioned inside the lumen of the nickel titanium tube and appended to the cylindrical inner wall.

3. The apparatus of claim 2, wherein the tubular insulative sleeve is formed to include a through lumen situated inside the lumen formed in the nickel titanium tube.

4. The apparatus of claim 1, wherein the nickel titanium tube is made of superelastic nitinol.

5. An apparatus comprising
   a flexible, elongated tubular member having a central axis extending longitudinally therethrough,
   a tube made of temperature-activated shape memory material and formed to include a lumen extending therethrough, the tube being arranged to lie inside the tubular member and positioned to cause the lumen to extend along the central axis of the tubular member, and
   control means for selectively heating the tube made of shape memory material to move the tube to assume a predetermined shape, thereby moving the tubular member so that it assumes a corresponding predetermined shape.

6. The apparatus of claim 5, wherein the temperature-activated shape memory material is nickel titanium.

7. The apparatus of claim 5, wherein the tube includes a cylindrical inner wall defining the boundary of the lumen and the apparatus further comprises a tubular insulative sleeve positioned inside the lumen of the tube and appended to the cylindrical inner wall.

8. The apparatus of claim 7, wherein the tubular inner sleeve is formed to include a through lumen situated inside the lumen formed in the tube.

9. The apparatus of claim 5, wherein the tubular member includes an outer sleeve around the tube and an inner sleeve inside the lumen formed in the tube.

10. The apparatus of claim 9, wherein the inner sleeve is formed to include a through lumen extending along the central axis of the tubular member.

11. The apparatus of claim 9, wherein the tube includes a cylindrical outer wall defining an outer surface of the tube and a cylindrical inner wall defining the boundary of the lumen, the outer sleeve is appended to the cylindrical outer wall, and the inner sleeve is appended to the cylindrical inner wall.

12. An apparatus comprising
    a flexible, elongated tubular member having a central axis extending longitudinally therethrough, and a tube made of superelastic nitinol and formed to include a lumen extending therethrough, the tube being arranged to lie inside the tubular member and positioned to cause the lumen to extend along the central axis of the tubular member.

13. The apparatus of claim 12, wherein the tubular member is formed to include an interior side wall defining a passageway extending longitudinally along the central axis therethrough and the tube includes an exterior side wall extending longitudinally along the central axis of the tubular member and engaging the interior side wall of the tubular member.

* * * * *